(12) United States Patent
Bickmeyer et al.

(10) Patent No.: US 8,198,098 B2
(45) Date of Patent: Jun. 12, 2012

(54) OPTICAL MEASUREMENT METHOD FOR DETERMINING THE PH OF A MEDIUM USING AGELADINE A AS A FLUORESCENT PH INDICATOR

(75) Inventors: Ulf-Georg Bickmeyer, Bremerhaven (DE); Karl-Walter Klings, Helgoland (DE); Achim Grube, Laupheim (DE); Matthias Koeck, Frankfurt (DE)

(73) Assignee: Stiftung Alfred-Wegener-Institut fuer Polar-und Meeresforschung, Bremerhaven (DE)

( * ) Notice: Subject to any disclaimer, the term of this patent is extended or adjusted under 35 U.S.C. 154(b) by 394 days.

(21) Appl. No.: 12/601,908

(22) PCT Filed: Apr. 1, 2008

(86) PCT No.: PCT/DE2008/000570
§ 371 (c)(1),
(2), (4) Date: Nov. 25, 2009

(87) PCT Pub. No.: WO2008/145080
PCT Pub. Date: Dec. 4, 2008

(65) Prior Publication Data
US 2010/0178664 A1    Jul. 15, 2010

(30) Foreign Application Priority Data

May 28, 2007 (DE) .......... 10 2007 024 985
Jul. 15, 2007 (DE) .......... 10 2007 034 886

(51) Int. Cl.
*G01N 31/16* (2006.01)

(52) U.S. Cl. ........ 436/163; 436/164; 436/166; 436/169; 436/172; 422/82.05; 422/82.06; 422/82.07; 422/82.08

(58) Field of Classification Search ........................ None
See application file for complete search history.

(56) References Cited

U.S. PATENT DOCUMENTS

| | | | |
|---|---|---|---|
| 4,945,171 A | 7/1990 | Haugland et al. |
| 5,567,624 A | 10/1996 | Smith |
| 6,391,626 B1 | 5/2002 | Adams et al. |
| 2006/0154296 A1 | 7/2006 | Miyawaki et al. |

FOREIGN PATENT DOCUMENTS

| | | |
|---|---|---|
| DE | 2560064 C3 | 12/1983 |
| DE | 3923921 A1 | 1/1991 |
| DE | 19681363 C2 | 7/2002 |
| DE | 10152994 A1 | 8/2003 |
| DE | 102004002885 A1 | 8/2005 |
| DE | 60013613 T2 | 9/2005 |
| EP | 1512745 A1 | 3/2005 |

OTHER PUBLICATIONS

Assmann et al., Chemical defenses of the Caribbean sponges *Agelas wiedenmayeri* and *Agelas conifer*, Mar. Ecol. Prog. Ser., 2000, vol. 207, pp. 255-262.

(Continued)

*Primary Examiner* — Yelena G Gakh
*Assistant Examiner* — Robert Xu
(74) *Attorney, Agent, or Firm* — Leydig, Voit & Mayer, Ltd.

(57) ABSTRACT

An optical measurement method for determining a pH of a medium includes adding a fluorescent pH indicator to the medium. The pH indicator is based on naturally-obtained or synthesized ageladine A. The pH indicator is irradiated with light of at least one wavelength so as to provide fluorescence excitation of the pH indicator. An emitted fluorescence intensity of the pH indicator is detected as a measure for the pH of the medium.

9 Claims, 5 Drawing Sheets

OTHER PUBLICATIONS

Bickmeyer et al., Disturbance of Voltage Induced Cellular Calcium Entry by the Marine Pyrrole-Imidazole Alkaloids Massadine, Mauritiamine, Stylissadines A and B, Tetrabromostyloguanidine and Dibromopalau amine, Toxicon, 2007, vol. 50, pp.. 490-497.

Fujita et al., Ageladine A: An Antiangiogenetic Matrixmetalloproteinase Inhibitor from Marine Sponge *Agelas nakamurai*, J. Am, Chern. Soc., 2003, vol. 125, pp. 15700-15701, XP008094136.

Fujita et al., Supporting Information for Ageladine A: an Antiangiogenic matrixmetalloproteinase inhibitor from the Marine Sponge *Agelas nakamurai*, 2003.

Meketa et al., A New Total Synthesis of the Zinc Matrixmetalloproteinase Inhibitor Ageladine A Featuring a Biogenentically Patterned 6-Pi-2-Azatriene Eiectrocyclization, Org. 6-Pi-2-Azatriene Electrocyclization. Org. Lett., 2007, vol. 9, No. 5, S. 853-855.

Meketa et al., Total Synthesis of Ageladine A, an Angiogenesis Inhibitor from the Marine Sponge *Agelas nakamurai*, Org. Lett. 2006,8,7, pp. 1443-1446.

Shengule et al., Concise Total Synthesis of the Marine Natural Product Ageladine A, Org. Lett., 2006, vol. 8, No. 18, pp. 4083-4084.

wo

US 8,198,098 B2

OPTICAL MEASUREMENT METHOD FOR DETERMINING THE PH OF A MEDIUM USING AGELADINE A AS A FLUORESCENT PH INDICATOR

CROSS REFERENCE TO PRIOR APPLICATIONS

This application is a U.S. National Phase application under 35 U.S.C. §371 of International Application No. PCT/DE2008/000570, filed on Apr. 1, 2008, and claims benefit to German Patent Application Nos. DE 10 2007 024 985.5, filed on May 28, 2007 and DE 10 2007 034 886.1, filed on Jul. 15, 2007. The International Application was published in German on Dec. 4, 2008 as WO 2008/145080 under PCT Article 21(2).

FIELD

The present invention relates generally to pH measurement and more specifically to an optical measurement method for determining the pH of a medium by addition of a fluorescent pH indicator.

BACKGROUND

The hydrogen concentration, or the pH, is an extremely important parameter in biological and chemical/technical systems. Many chemical and biological reactions require an exact regulation of the pH for a proper course. For example, a complex natural process takes place for regulating the pH in human blood, which normally has a pH of approximately 7.4. Even changes of just a few tenths of a pH unit can be due to or cause serious disease states. Although a multiplicity of techniques has been developed to measure pH, these are generally based on either electrochemical or optical principles. A standard laboratory pH measurement device, for example comprises a standard electrode of known electric potential, a special glass electrode which changes electric potential as a function of the concentration of hydrogen ions in the medium into which it is being dipped and a potentiometer which measures the electric potential between the two electrodes, from which a numerical pH is determined. Methods of this type are not however very good for measurements in intact biological systems, as a measurement electrode needs to be inserted.

In the context of optical measurements, pH indicators are used, which pH indicators are dyes whose detectable optical characteristics, such as extinction (absorption) or fluorescence likewise change with the change of the pH. Thus, pH indicators indicate the current pH of the solution by means of their color shade and their color intensity. The greatest sensitivity of indicators to small changes of pH is present if the equilibrium constant ($pK_a$) between the acidic and basic forms of the indicator is close to the pH of the medium to be investigated, generally a solution.

As a broad generalization, optical measurements of the pH are regarded as being inferior to the electrochemical techniques, mainly because factors different from the hydrogen ion concentration, such as temperature, ionic strength and protein concentration can influence the dyes and interfere with the pH measurements. Nevertheless, optical techniques have enormous advantages when costs and size play a role and especially when the pH should be measured in living cells and tissues, into which no measurement probe can be inserted. Measurements of pH-dependent emission intensity in individual cells with a single excitation wavelength suffer from inaccuracies which relate to dye concentration, photobleaching of the dye, thickness of the cell measured or path length. A solution of the problem of dye concentration consists in the determination of the ratio of the fluorescence intensity at a fixed wavelength with excitation at a pH-sensitive wavelength to fluorescence intensity at the same wavelength with excitation at a relatively pH-insensitive wavelength. This method is usually used in order to estimate the pH in the interior of cells with fluorescence derivatives and is suitable in practice for suspensions of cells and in homogeneous liquids, such as media in a research fluorometer or microscope.

An optical biosensor is described in DE 39 23 921 A1, in the case of which biosensor an enzyme which catalyses a chemical reaction is bonded to a pH indicator. The indicator can be a fluorescent dye, particularly one based on coumarin. A change of the pH during the chemical reaction can be determined due to measurable change of the fluorescence intensity of the dye. A culture medium for the detection and the determination of numbers of microorganisms is described in DE 600 13 613 T2, which culture medium comprises a pH indicator which is chemically bonded to a hydrophilic substance with a high molecular weight. Thus, a water-soluble pH indicator with ballast is provided, which at the same time, as a nutrient gel, supports the hydrated growth of the microorganisms. Growth detection is brought about by the detection of the change in fluorescence of the pH indicator, which can contain carboxyphenol red, in the culture medium. DE 101 52 994 A1 describes an optical method for the simultaneous determination of pH and dissolved oxygen. To this end, two fluorescent, for example, ruthenium-based, pH indicators are used in a common matrix in the medium.

A pH indicator based on fluorescent xanthine dyes is described in U.S. Pat. No. 4,945,171. Here, two emission maxima are measured during the excitation with just one wavelength with particular selectivity for the independent excitation of acid and base form at either a single or two wavelength(s) and the pH-dependent absorption or fluorescence excitation spectra resulting therefrom. A pH indicator based on fluorescent carbazine dyes and derivatives is described in DE 196 81 363 C2. Carbazine dyes exhibit greater fluorescence, greater stability, greater temperature sensitivity and greater Stokes shifts compared to xanthine dyes. Additionally, the carbazine dyes are better to immobilize on a solid support. A method for indicating the pH of a solution as medium is disclosed, in the case of which the pH indicator is added to the solution and brought into contact with light of a chosen wavelength, in order to excite the carbazine dye to fluorescence, the intensity of the fluorescence at two different wavelengths is measured and the ratio of the fluorescence intensities at the two chosen wavelengths is calculated and the ratio is correlated with a predetermined relationship for such ratios with the pH.

Further fluorescent dyes which are used for measuring pH are, for example, the dyes BCECF and DNP-160. Further molecular probes from the pH indicator family can, for example, be drawn from the following table (sorted by descending equilibrium constant $pK_a$, tables taken from http://probes.invitrogen.com/handbook/tables/0361.html, as of 27.05.2007). The small size of the detectable pH range can be seen clearly in each case.

| PRECURSOR FLUOROPHORE | PH RANGE | TYPICAL MEASUREMENT |
| --- | --- | --- |
| SNARF indicators | 6.0-8.0 | Emission rate 580/640 nm |
| HPTS (pyranine) | 7.0-8.0 | Excitation rate 450/405 nm |
| BCECF | 6.5-7.5 | Excitation rate 490/440 nm |

| PRECURSOR FLUOROPHORE | PH RANGE | TYPICAL MEASUREMENT |
|---|---|---|
| Fluoresceins and carboxyfluoresceins | 6.0-7.2 | Excitation rate 490/450 nm |
| LysoSensor Green DND-189 | 4.5-6.0 | Individual emission 520 nm |
| Oregon green dyes | 4.2-5.7 | Excitation rate 510/450 nm or 490/440 nm |
| LysoSensor yellow/blue DND-160 | 3.5-6.0 | Emission rate 450/510 nm |

The bioactive natural marine substance ageladine A (chemical formula $C_{10}H_7N_5Br_2$) is a pyrrole-imidazole alkaloid, which can be isolated from sponges of the genus *Agelas* for example (cf. Publication I by M. Fujita et al.: "Ageladine A: An Antiangiogenetic Matrixmetalloproteinase Inhibitor from Marine Sponge *Agelas nakamurai*", J. Am. Chem. Soc. 2003, 125, 15700 ¬15701 and Supporting Information S.I. 1-15). Ageladine A can meanwhile also be completely synthesized (cf. Publication II by M. Meketa et al.: "Total Synthesis of Ageladine A, an Angiogenesis Inhibitor from the Marine Sponge *Agelas nakamurai*" Org. Lett. 2006, 8, 7, 1443¬1446, Publication III BY S. Shengule et al.: "Concise Total Synthesis of the Marine Natural Product Ageladine A", Org. Lett. 2006, 8, 18, 4083-4084 and Publication IV by M. Meketa et al.: "A New Total Synthesis of the Zinc Matrixmetalloproteinase Inhibitor Ageladine A Featuring a Biogenetically Patterned 6πt-2-Azatriene Electrocyclization", Org. Lett. 2007, 9, 5, 853-855). Thus, ageladine A is publicly available in an unlimited amount. In scientific investigations of ageladine A with measurements for the cellular action of natural marine substances, ageladine A exhibits a disruptive autofluorescence (cf. Publication V by U. Bickmeyer et al.: "Disturbance of Voltage Induced Cellular Calcium Entry by the Marine Pyrrole-Imidazole Alkaloids", doi:10.1016/j.toxicon.2007.04.015). Following UV excitation, ageladine A has a pronounced fluorescence in the green range (see Publication I).

DE 10 2004 002 885 B4 describes a range of new bioactive compounds from the class of pyrrole alkaloids. In this case, marine sponges are a rich source of pyrrole alkaloids, a group of natural substances which stands out on account of its structural variety and interesting biological activities. Mention is also made of pyrrole-imidazole alkaloids obtained from various Caribbean sponge species of the genus *Agelas*, with a selective antihistaminic effect and Agelongin (structural formula 22) from *Agelas longissima* with an antiserotonergic effect on fundus preparations from rat stomachs. All bioactive compounds mentioned are used exclusively for medical purposes, particularly for combating neurodegenerative diseases.

SUMMARY

In an embodiment, the present invention provides an optical measurement method for determining a pH of a medium. A fluorescent pH indicator based on naturally-obtained or synthesized ageladine A is added to the medium. The pH indicator is irradiated with light of at least one wavelength so as to provide fluorescence excitation of the pH indicator. An emitted fluorescence intensity of the pH indicator is detected as a measure of the pH of the medium.

BRIEF DESCRIPTION OF THE DRAWINGS

The optical measurement method for determining the pH of a medium using ageladine A as a fluorescent pH indicator is explained in more detail for the further understanding of the invention in the following on the basis of the schematic figures. In the figures.

DETAILED DESCRIPTION

Figure 1A:
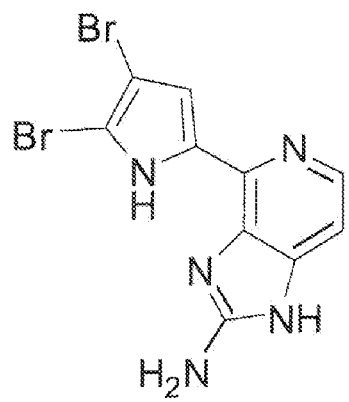
FIG. 1A shows the structural formula of ageladine A.

In an embodiment, the present invention provides a method of optical measurement for determining the pH of a medium in which an alternative fluorescent pH indicator is used. The alternative pH indicator shows a reduced sensitivity with respect to potentially disruptive factors and a large pH measurement range. In particular, a substantially improved measurement performance in biological systems, of which the majority operate in the range from pH5 to pH9, is provided according to an embodiment of the present invention.

In an embodiment, the present invention provides an optical measurement method for determining a pH of a medium by:

addition of a fluorescent pH indicator to the medium, fluorescence excitation of the pH indicator by means of irradiation of the pH indicator with light of at least one chosen wavelength and detection of the emitted fluorescence intensities of the pH indicator as a measure for the pH of the medium.

The optical measurement method according to an embodiment of the present invention includes an alternative fluorescent pH indicator based on ageladine A. Ageladine A is a known natural marine substance in the form of a pyrrole-imidazole alkaloid which has heretofore been used exclusively for medical purposes. Ageladine A can be obtained both from marine sponges and produced synthetically. It is therefore readily possible, by means of the total syntheses described, to prepare large quantities of ageladine A without having to have recourse to marine sponges. To use ageladine A in the context of the present invention, the autofluorescence which occurs can be used for measurement purposes by means of excitation amplification by means of irradiation with light in the UV range between wavelengths of 315 nm and 400 nm. Ageladine A shows a marked fluorescence in the green range between wavelengths of 490 nm and 575 nm. When using ageladine A as a fluorescent pH indicator, pH changes of the medium to be investigated between pH4 and pH9 can be reliably optically indicated by means of a changeable fluorescence intensity in such a manner that the emitted fluorescence intensity increases as the pH falls. The pH range which can be indicated by ageladine A is unusually large for a fluorescent pH indicator and the stainings prove to be very temporally stable.

The fluorescent characteristics of molecules can be traced back to their chemical structure. In this case, the following general points should be fulfilled by the chemical molecule structure: aromatic or delocalised Π-electron system, chromophore, rigid and planar molecular structure. All of these points are fulfilled by the molecular structure of ageladine A. The structure has an aromatic system (pyrrole, pyridine) as well as the Π-electron system of guanidine. Due to the basic guanidine structure, protonation is very probable at this point in acidic media. The positive charge arising as a result can be delocalised over the entire molecule in the process, which is a prerequisite for a chromophoric system. The formulated boundary structure has a rigid and planar molecular structure. The fluorescent properties and also pH-dependent changes in the fluorescence can therefore be explained (cf. FIGS. 1A, 1B).

It has surprisingly furthermore been found that ageladine A shows a particularly high sensitivity of emitted fluorescence intensity in the physiologically relevant range between pH6 and pH8. Thus, ageladine A can be used particularly well as a pH indicator for physiological pH measurements. Advantageously, samples that have been taken (in vitro), but also living cells, tissue and entire organisms (in vivo) can be incubated with ageladine A as fluorescent pH indicator and stained in this manner by means of the fluorescence in the green range. This enables measurements of the pH in vivo and in vitro in a wide range and thus the detection of acidic tissue in organisms due to its fluorescence properties. The fluorescence in the green range increases markedly as the pH falls. The intensive stainings prove to be stable over hours to days.

With the method according to an embodiment of the present invention, pH measurements of solutions and pH measurements within living cells, tissues and entire organisms as medium can therefore be carried out using ageladine A as a fluorescent pH indicator. A fluorescent staining of cells and tissues by means of incubation of these media with ageladine A is possible. Advantageously, an in-vivo or in-vitro incubation of cells, tissues or entire organisms as medium in a solution containing the fluorescent pH indicator can take place. Acidic tissue portions (digestive organs) in living organisms can be marked and easily recognized under the fluorescence microscope by means of an easy, quick and biological staining of this type. Ageladine A can therefore be utilized as an exceptionally intensive cell dye which reproducibly indicates pH changes as a pH indicator. Qualitative pH changes and quantitative pH measurements within living systems can be strongly simplified by means of the invention.

The method according to an embodiment of the present invention with use of ageladine A as a pH indicator shows the following particular advantages:
 Easy handling. Due to full synthesis, the natural marine substance ageladine A is available in large quantities, without endangering species protection.
 Great sensitivity of ageladine A in the physiologically particularly interesting range between pH6 and pH8.
 fluorescence is stable for hours despite UV irradiation. The stainings last for at least a plurality of days.
 Short-term incubation of cells and tissues with ageladine A leads to a clearer and stronger fluorescence.
 Even intact, living organisms can be stained with ageladine A, as it penetrates very quickly and far into the tissue on account of its lipophilic structure (bromination).
 Acidic constituents of organisms can be immediately detected at a glance, following incubation, in the fluorescence microscope since the fluorescence increases greatly as the pH falls.

Various interfering factors can affect the pH measurements negatively, if applicable, if measuring is only carried out at a single excitation wavelength. Therefore, the method according to various embodiments of the present invention using ageladine A as fluorescent pH indicator can be advantageously provided with one or more of the following features:
 a fluorescence excitation at two chosen wavelengths;
 detection of the emitted fluorescence intensities;
 calculation of the ratio of the fluorescence intensities; and
 correlation of the ratio with a predetermined relationship for such ratios with the pH of the solution.

Figure 1B:
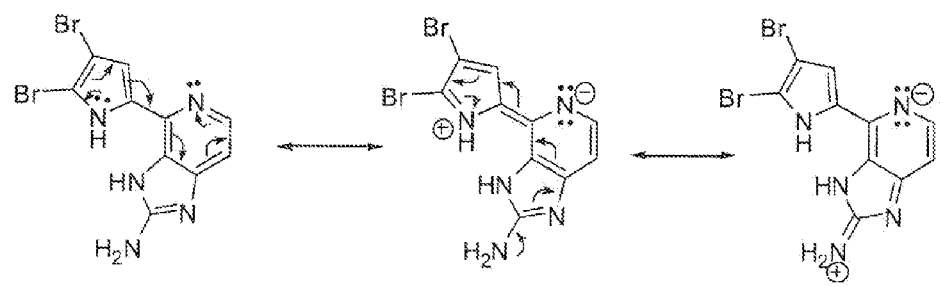
FIG. 1B shows the protonation and stabilisation of ageladine A.

The structural formula of ageladine A can be drawn from FIG. 1A. FIG. 1B shows the protonation of the guanidine group in ageladine A and the stabilization of the positive charge over the entire structure. The right structure contains a rigid and planar arrangement which among other things is responsible for the fluorescence.

Figure 2A:
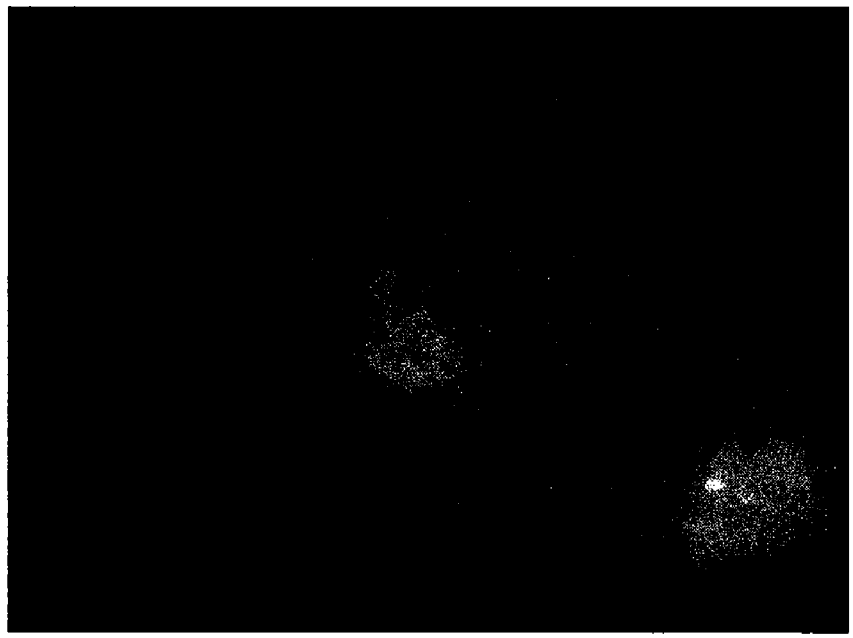
FIGS. 2A and 2B show fluorescence of cells stained with ageladine A.
Figure 2B:
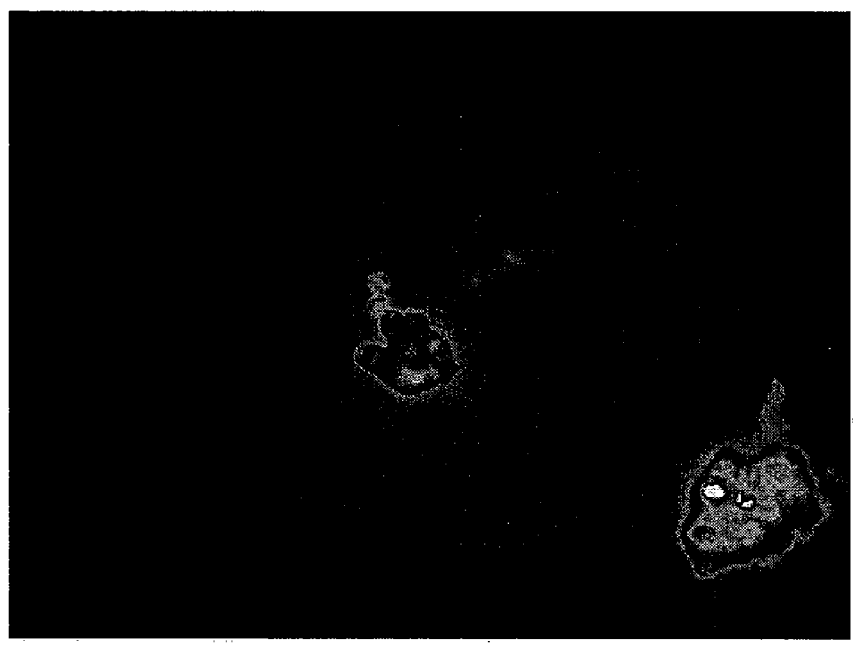

FIGS. 2A, 2B show images, at 400-times magnification, of cells (PC-12 cells, rat, deposited at DSMZ) incubated with ageladine A and stained by means of the same. Excitation took place using UV light with a wavelength of 380 nm.

Figure 3:
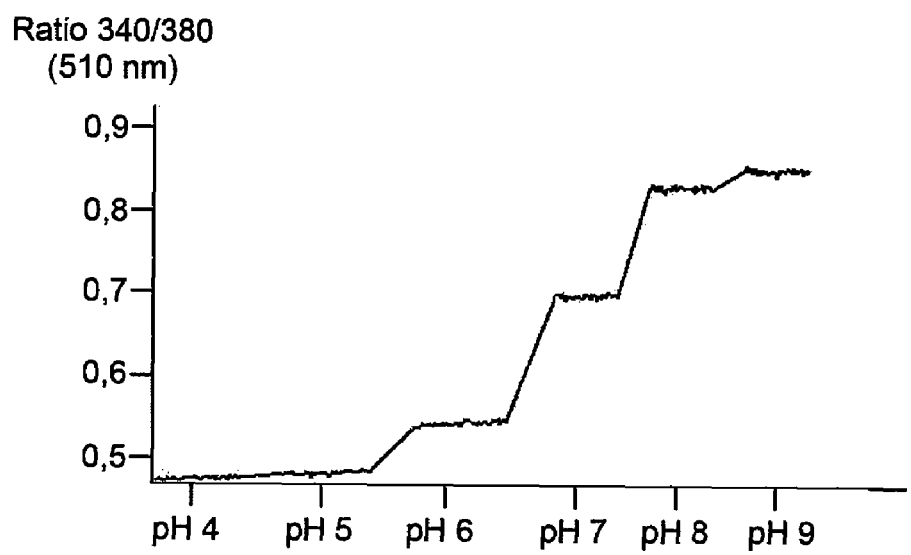
FIG. 3 shows the fluorescence intensity diagram of ageladine A as a function of the pH.

FIG. 3 shows the fluorescence ratio value (measured during a fluorescence emission at 510 nm) of the excitation wavelengths 340 nm/380 nm at various pH values for an addition of 20 μM ageladine A into a physiological buffer. The measurable large pH range with a good assignability of the measured ratio values to the individual pHs can be clearly recognized.

Figure 4:
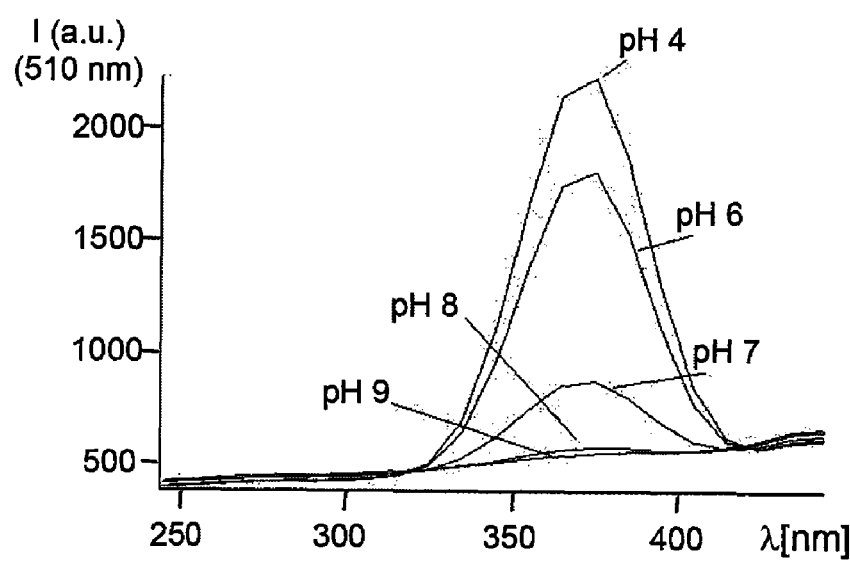
FIG. 4 shows the excitation spectrum of ageladine A as a function of the pH.

FIG. 4 shows the excitation spectrum (emitted fluorescence intensity over the excitation wavelength in nm) of ageladine A at various pHs of the solution. The fluorescence intensity was measured at 510 nm. The great pH sensitivity of ageladine A in the physiologically relevant range around pH7 can be recognized.

Figure 5:
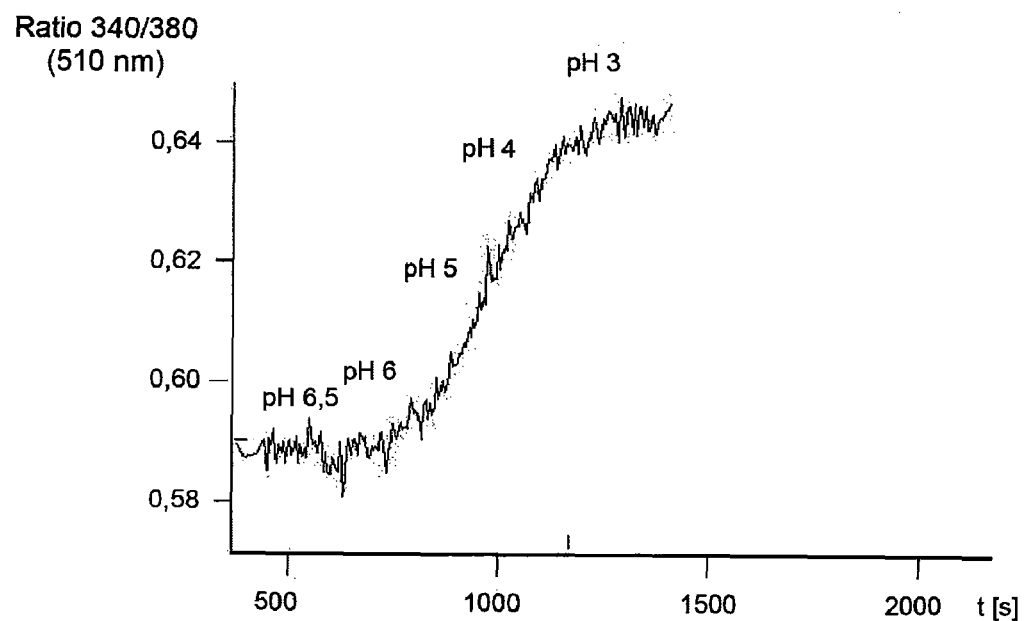
FIG. 5 shows measurements of the intracellular pH during the change of the extracellular pH.

FIG. 5 shows the measurement protocol of a measurement of the intracellular pH of PC12 cells by means of ageladine A in the case of the change of the external pH of the solution. The fluorescence ratio value (340 nm/380 nm) is plotted over time (time in s). The various pHs of the buffer solution are marked as parameters on the graph. It can clearly be recognized that the fluorescence emission follows the extracellular increase of the pH of the solution in a wide range (pH6.5 to pH3). The change of the intracellular pH is only a few tenths around pH7, as a result of which a very high measurement resolution of the pH indicator results.

Figure 6A:
FIG. 6A shows an organism (a shrimp)
Figure 6B:
FIG. 6B shows an in-vivo staining of the shrimp with ageladine A.

FIG. 6A shows a microscopic illuminated image from above of a living organism, here a shrimp (*Palaemonetes argentinus*), at a magnification of 100 times. FIG. 6B shows the fluorescence image of this shrimp after it was incubated with ageladine A and irradiated with UV light. On account of the intensity of the emitted fluorescence, it can be recognized that acidic structures (mouth-digestive region) in the shrimp were stained.

Figure 7:
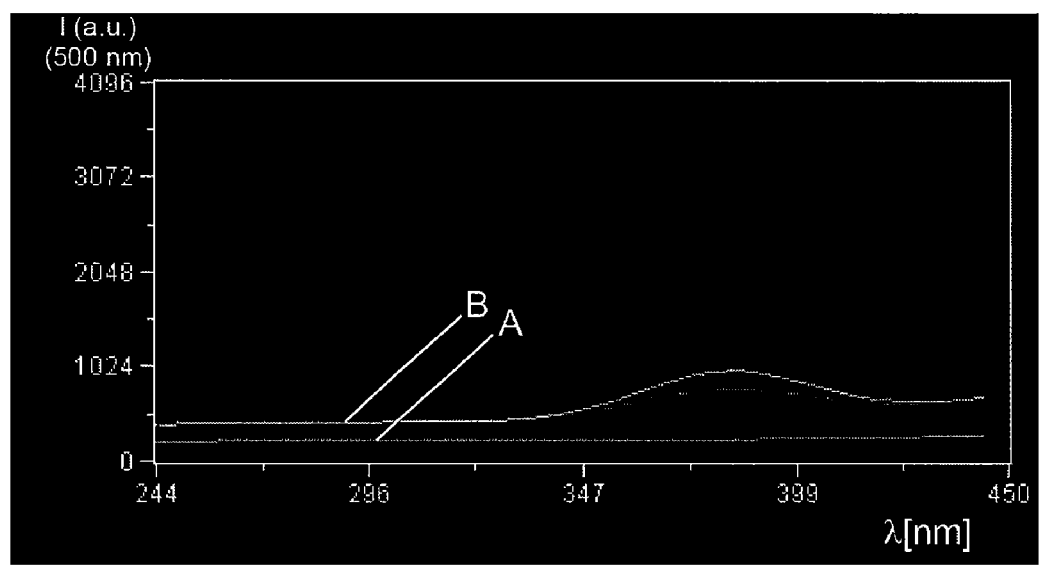
FIG. 7 shows the excitation spectrum of ageladine A in the shrimp.

FIG. 7 shows the excitation spectrum (emitted fluorescence intensity over the excitation wavelength) of ageladine A in the shrimp in the mouth-digestive region, measured at 510 nm fluorescence emission. The green curve (lowest straight curve) indicates fluorescence intensity values within the buffer solution outside of the shrimp, the red and blue curves (middle and upper curved curves) indicate fluorescence intensity values within the shrimp and thus, in a simple manner, easily recognizable and detectable acidic constituents of the shrimp.

While the invention has been particularly shown and described with reference to preferred embodiments thereof, it will be understood by those skilled in the art that various changes in form and details may be made therein without departing from the spirit and scope of the invention.

The invention claimed is:

1. An optical measurement method for determining a pH of a medium, the method comprising:
   adding a fluorescent pH indicator to the medium, the fluorescent pH indicator being based on naturally-obtained or synthesized ageladine A;
   irradiating the pH indicator with light of at least one wavelength so as to provide fluorescence excitation of the pH indicator; and
   detecting an emitted fluorescence intensity of the pH indicator as a measure of the pH of the medium.

2. The optical measurement method according to claim 1, wherein the pH indicator has a fluorescence in the green range between wavelengths of 490 nm and 575 nm when the irradiating is performed with light in the UV range between wavelengths of 315 and 400 nm.

3. The optical measurement method according to claim 1, wherein the pH indicator has a high sensitivity of the emitted fluorescence intensity in a physiologically particularly relevant region between pH6 and pH8.

4. The optical measurement method according to claim 1, wherein pH changes of the medium between pH4 and pH9 are optically indicated by a changeable fluorescence intensity, wherein the emitted fluorescence intensity increases as the pH decreases.

5. The optical measurement method according to claim 1, wherein the medium includes at least one of an in-vivo or in-vitro incubation of cells, tissues and entire organisms.

6. The optical measurement method according to claim 5, wherein the adding the fluorescence pH indicator is performed so as to provide the medium in a solution containing the fluorescence pH indicator.

7. The optical measurement method according to claim 5, further comprising observing the incubated medium in a fluorescence microscope.

8. The optical measurement method according to claim 1, wherein the at least one wavelength includes a first and a second wavelength and the emitted fluorescence intensity of the pH indicator is detected at each of the wavelengths, and wherein the method further comprises calculating a ratio of the emitted fluorescence intensities and correlating the ratio with a predetermined relationship with the pH of the medium.

9. The optical measurement method according to claim 1, wherein the at least one wavelength is 365 nm.

* * * * *